United States Patent [19]

Gerez et al.

[11] Patent Number: 4,529,699

[45] Date of Patent: Jul. 16, 1985

[54] PROCESS AND INSTALLATION FOR OBTAINING ETHANOL BY THE CONTINUOUS ACID HYDROLYSIS OF CELLULOSIC MATERIALS

[75] Inventors: Jose C. C. Gerez; Maria D. C. A. Gerez; Joseph Miller, all of Campinas, Brazil

[73] Assignee: Industrias Villares S.A., Brazil

[21] Appl. No.: 372,105

[22] Filed: Apr. 27, 1982

[30] Foreign Application Priority Data

Apr. 30, 1981 [BR] Brazil ................................. 8102802

[51] Int. Cl.$^3$ .............................................. C12P 7/10
[52] U.S. Cl. ........................................ 435/165; 435/163
[58] Field of Search ............... 435/161, 163, 165, 813; 426/626, 807; 127/37

[56] References Cited

U.S. PATENT DOCUMENTS

| | | | |
|---|---|---|---|
| 1,857,429 | 5/1932 | Christensen | 435/163 |
| 2,086,701 | 7/1937 | Dreyfus | 435/163 X |
| 2,222,885 | 11/1940 | Thomsen | 435/163 |
| 4,201,596 | 5/1980 | Church et al. | 435/163 X |
| 4,342,831 | 8/1982 | Faber et al. | 435/163 |

*Primary Examiner*—R. B. Penland
*Attorney, Agent, or Firm*—Darby & Darby

[57] ABSTRACT

Invention patent for a "Process and Installation for Obtaining Ethanol by the Continuous Acid Hydrolysis of Cellulosic Materials", such process comprising the stages of: providing an homogenized aqueous pulp of cellulosic material having 3 to 30% in weight of solids; pumping the cellulosic material pulp, in a substantially continuous way, to the interior of the inlet end of a tubular reactor and restricting its outlet opposite end to maintain a given internal pressure inside the same; heating the pressurized cellulosic material pulp up to the temperature of about 160° to 250° C. before its introduction into the reactor; adding, in a substantially continuous way, a given dose of a concentrated acid to the pressurized and heated cellulosic material pulp, which will be continuously diluted in the reactor, to provide the hydrolysis reaction of said pulp, the acid addition being made inside the reactor at a point longitudinally adjustable from the inlet end of the reactor; discharging in a substantially continuous way through the outlet end of the reactor a given load of hydrolyzed cellulosic material, said discharge being regulated in conjunction with the longitudinal positioning of the point of addition of the acid, thus fixing the reaction time adequate for the cellulosic material pulp; subjecting the hydrolyzed cellulosic material pulp to an abrupt pressure drop and cooling immediately after it leaves the reactor; neutralizing and fermenting the resulting aqueous solution to obtain ethanol; and recovering the resulting byproducts which are methanol, furfural, acetic acid and lignin.

3 Claims, 1 Drawing Figure

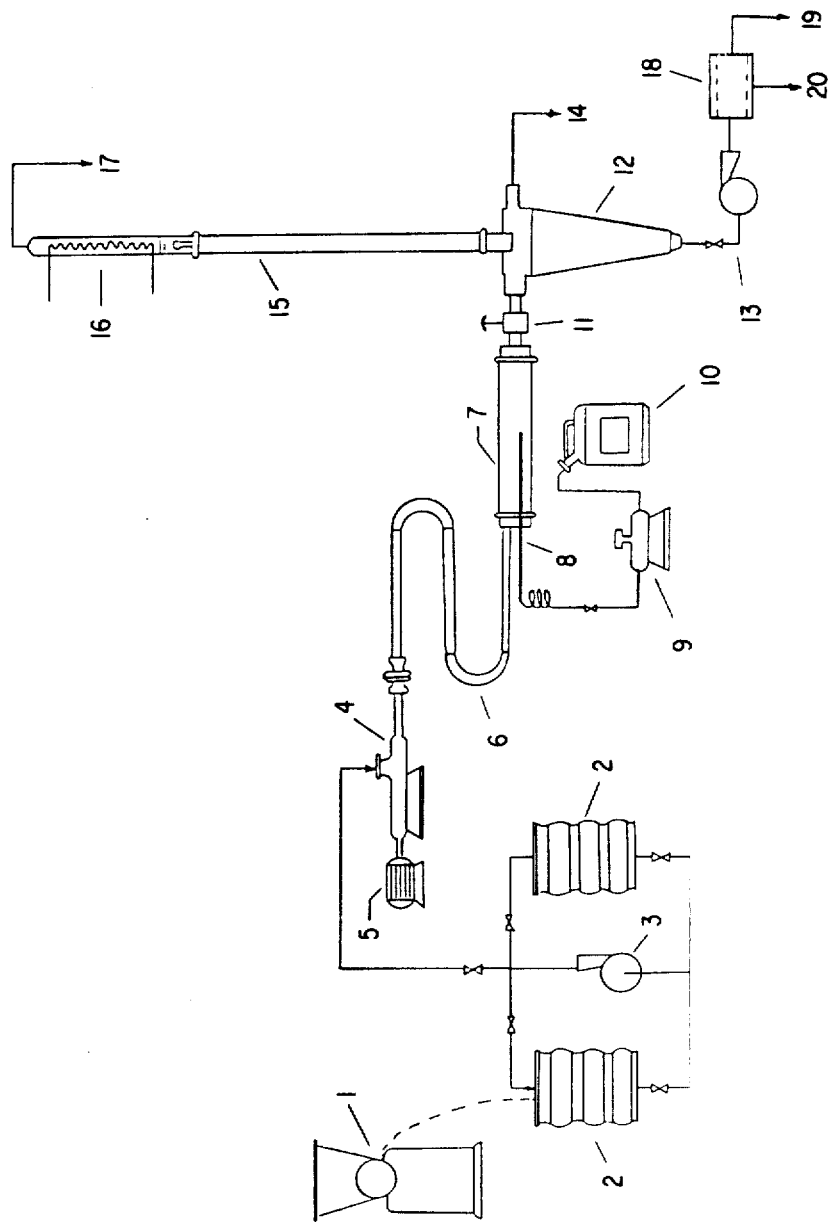

PROCESS AND INSTALLATION FOR OBTAINING ETHANOL BY THE CONTINUOUS ACID HYDROLYSIS OF CELLULOSIC MATERIALS

This invention refers to a process and installation for obtaining ethanol as a liquid Fuel by continuous acid hydrolysis of celulosic materials, such as wood, forest residues, agricultural residues, urban garbage and others, thus making possible the industrial utilisation of said cellulosic materials in high yield and productivity and with low investment, the latter being particularly true of agricultural residues, to produce ethanol, single cell protein, lignin coke, furfural, methanol and acetic acid.

Acid hydrolysis of cellulosic materials and the subsequent fermentation of the hydrolysate to obtain ethanol has been considered as a serious alternative to produce ethanol on a large scale to achieve the aims related to the production of carburetant alcohol from sugar cane. Such an alternative creates the possibility of exploiting lands less appropriate for the production of sugar cane and, due to the resulting byproducts, it could also meet other needs, it being possible, for instance, to obtain metallurgical coke of good quality from lignin, and unicellular proteins for the animal food industry from pentose fermentation. Also, furfural, methanol and acetic acid are important products on the domestic and international market. The production of alcohol, via acid hydrolysis of agriculture residues, besides creating another alternative for the production of alcohol and thus, avoiding excessive dependence on sugar cane, could expand agricultural and cattle raising activities with which it maintains a complementary relationship. For example, lignin can be used to improve the soil, considering that it is an improtant constituent of humus and has a great capacity to retain humidity and, in addition to being resistant to decomposition by microorganisms, a quality which confers upon an extended action; it is also important in its considerable capacity to absorb neutral salts, thus allowing the retention of fertilizers and their subsequent gradual release thereof. Another possibility arises from the aerobic fermentation of the hydrolyzed product to produce unicellular protein which can be complemented to suit the needs of the stock raising industry. Also, it is important to point out that the basic nutrients contained in the processed residue can be recovered and returned to the soil.

The traditional raw material for the production of fermentable sugars by hydrolysis has been wood.

However, due to their particular physical properties, in addition to clear economic advantages, agriculture residues can perform a very important role in the field of saccharification. A limiting factor in the process of saccharification is the low rate of diffusion through the wood of the sugar solution but the porous characteristics of agricultural residues eliminates this factor. So, a continuous process of acid hydrolysis would have more success when applied to agriculture residues.

Within the present context, ethanol is undoubtably the main product from the acid hydrolysis. It is obtained by fermentation of the hydrolyzed product.

However, a number of other products could be obtained by different fermentation routes. Among them, are the following: acetic acid, butyric acid, lactic acid and citric acid, acetone, butylene glycol and glycerol.

The duration of hydrolysis being extended, pentoses can be turned into furfural and hexoses into levulinic acid. The second most predicted use for the hydrolyzed product is its transformation into animal feed by fermentation. Depending upon the type and the conditions of the fermentation, such feeds could be rich in carbohydrates, rich in vitamins or could contain up to 50% protein. For example, with "Torula utilis", it is possible to obtain, from 1000 kg of dry residue, 250 kg of feed containing 45-50% protein, 5-8% carbohydrates and a high content of B group vitamins.

An important byproduct from hydrolysis is lignin which represents 20-30% in weight of the dry raw material. Due to its high content of carbon (65%) it has a high calorific value (5.800 kcal/kg of dry lignin) and it could be used to supply a part of the energy needs of the process.

On the other hand, lignin, by various chemical transformations (oxidation, hydrogenation, alkaline fusion, etc.) can be a source of a number of organic compounds.

The batch hydrolysis processes of cellulosic materials are grouped in two classes: hydrolysis with a concentrated acid (hydrochloric, sulphuric, fluorhydric and phosphoric) or, with a dilute acid (sulphuric, sulphurous, hydrochloric, etc).

A disadvantage of those processes employing a concentrated acid is the use of substrates with a humidity lower than 1% to prevent dilution of the acid. This fact added to the corrosion problems that dictate expensive materials to recover the acid, support the option of the dilute-acid process.

Although the processes using a dilute acid do not present any of the above mentioned disadvantages they are not as good in terms of energy efficiency or productivity when the expenses necessary for the construction of the installation are taken into account.

In short, the batch hydrolysis processes have shown themselves to be unprofitable.

As a result of a better knowledge of the kinetics of saccharification, studies were initiated some time ago to develop a continuous process of acid hydrolysis. Compared with the batch hydrolysis processes frequently described in the literature, the continuous process requires a retention time of only minutes in the reactor instead of hours. Other advantages are: a better control of the operational variables allowing complete automation; a lower energy consumption and, therefore, a lower operational cost and, mainly, a lower investment.

On the other hand, a continuous process facilitates the separation of the cellulosic material into its principal components: lignin, hemicellulose and cellulose. This separation is based on the difference in hydrolysis rate between hemicellulose and cellulose. In practice, a prehydrolysis in relatively mild conditions would turn hemicellulose into the sugars that compose its structure and which would then be removed by filtration and washing. Then, a vigorous hydrolysis at high temperatures would turn cellulose into glucose, which in a similar fashion would be removed from the lignin residue.

Although the known continuous acid hydrolysis processes have the above mentioned advantages in relation to the batch acid hydrolysis processes, they continue to exhibit some characteristics which tend to increase the costs involved in the construction and operation of the corresponding installations. Such continuous acid hydrolysis processes generally require a complex and expensive construction for the reactor which includes, besides its own reaction zone, zones for heating and pressurization or pumping of the material to be hydrolized. Even in the cases in which pressurization or pumping takes place prior to the reactor, the heating of the mixture to be hydrolyzed takes place in the reactor through steam injection, thus making it difficult to control the temperature and the concentration of the solids in the mixture and there is still not any provision for variation of the length of the reaction zone.

In short, it can be said that the known continuous acid hydrolysis processes require installations presenting severe restrictions as far as energy consumption or investment in equipment or the control of operational variables is concerned.

It is therefore an object of the present invention to promote a process and installation to obtain ethanol by means of a continuous acid hydrolysis of cellulosic materials, particularly of agriculture residues, by using equipment relatively simple, with a low cost, available on the domestic market and which allows better control of the operational variables, complete automation and a lower energy comsumption. According to the process of this invention, a certain quantity of cellulosic material is previously submitted to a comminution to achieve an appropriate granulometry, and afterwards, is subjected to homogenization with water to form a cellulosic material in water suspension or pulp, in those cases in which the addition of water is required. If the raw material is already an homogenized pulp of cellulosic matter it is evident that an homogenization stage prior to the acid hydrolysis will not be necessary.

Such previous homogenization is indispensable to achieve the results intended of the hydrolysis when the cellulosic pulp or suspension is made by addition of water to the dry ground cellulosic material. The desired concentration of solids in the mixture depends upon the type of material and its granulometry, being in the range of from 3 to 30% in weight. The homogenized cellulosic pulp is then continuously pumped at a pressure of between 10 to 40 kg/cm$^2$ at substantially constant flow, to be heated at a temperature of about 160° C. to 250° C., and fed to a tubular reactor, where it stays for a short period of time to receive the addition of a certain dose of a concentrated acid (preferably sulphuric acid) which, when contacting the mixture is diluted by the water present to reach a final concentration of about 0.1 to 3%.

At the outlet of the reactor a "flash" system is provided where a restriction, or expansion valve, will maintain constant the reactor internal pressure.

On passing through the expansion valve, the mixture passes abruptly from the reaction pressure to atmospheric pressure, being cooled down by its own evaporation in the process, thus completing the hydrolysis reaction. The solution obtained, herein called hydrolyzed product, contains, in the liquid portion, sugars (glycose, xylose, manose and arabinose) in addition to water and sulphuric acid.

The gaseous portion contains, besides water vapour, methanol, furfural and acetic acid which can be recovered. The solid portion of the solution obtained is basically composed of lignin.

The aqueous solution, after being neutralized, is converted into ethanol by known fermentation procedures. According to this new continuous acid hydrolysis process, the object of this invention, the reaction zone is separated from the means of heating and from the means of pumping the mixture, characteristics which result in the following advantages:

- at no time does the diluted acid enter in contact with any machine or movable part involved in the process, thus ensuring that the reactor and only the reactor is subjected to the most severe conditions of the hydrolysis;
- as the reactor is of a very simple conception, the use of two units per installation is provided for so that at anytime it will be possible to change this part rapidly without causing any interruption to the process;
- simplification in the concept of the reactor, which, because it is subject to severe conditions, must be constructed of a special alloy;
- simplification of the means of pumping the mixture, as such means are not subject to severe conditions;
- only the reation zone will be constructed of special alloy.

In addition to the characteristics above mentioned, this invention further provides for an acid injection system which allows the point where the same enters in contact with the mixture to be varied thus allowing a fine adjustment of the zone length or of the reaction time which, depending upon the material or upon the hydrolysis conditions, can vary from 20 to 300 seconds. Another advantage of the process in question, that is to say, a more stable control of the reaction temperature, arises from the fact that the heating of the mixture is effected in a separate stage prior to the reactor.

The process which is the object of this invention, will now be described in conjunction with a possible installation for its embodiment and reference is made to the annexed drawing the only FIGURE of which is a simplified flow sheet of the installation which would apply when agriculture residues were being used as a raw material.

According to the above mentioned illustration, a given quantity of cellulosic material is supplied to a grinder 1 of whatever type capable of conveniently effecting the comminution of the material to be hydrolyzed, which must attain a suitable granulometry for the purpose.

The cellulosic material is transferred from the grinder 1 to the means of mixing and homogenization which, in the example illustrated, will take the shape of a pair of homogenization tanks 2 where, by addition of water and circulation of the resulting mixture by means of the pump 3, an homogeneous pulp of cellulosic material is produced having a solids concentration varying between about 3 to 30% in weight, as a function of the nature and the granulometry of the cellulosic material. Tanks 2 operate alternatively to provide a continuous flow of cellulosic material. However, it must be understood that such tanks and the grinder could be dispensed with, if the raw material as supplied to the installation were already in the form of an homogeneous pulp of cellulosic material.

Pump 3 carries the mixture to a positive displacement pump 4 driven by a variable speed device 5. Such pump 4 can be of the type moino, screw, piston, membrane, spindle or even an extruder.

The positive displacement pump 4 allows pumping of the mixture at a pressure of between 10 to 40 kg/cm$^2$ and with a flow substantially constant, propelling the same through a heater 6 and into the tubular reactor 7, in which the acid hydrolysis will be effected.

Heater 6 will use direct injection of steam or will be in the form of any heat exchanger, using electricity, steam, pressurized hot water, oil or any other element, capable of raising the mixture to a temperature in the range of 160° C. to 250° C.

Reactor 7 is made up of a cylindrical tube of a special alloy such as, for instance, Hastelloy B, having one of the end flanges the mixture inlet flange fitted with means to permit the passage of and support the sulphuric acid injection tube 8.

The concentrated sulphuric acid is fed from the reservoir 10 by a pump 9.

The extent of penetration of the tube 8 into the reactor 7 is adjustable to vary the retention time of the reaction, thus allowing a fine adjustment of the said time for different processing situations. It is clear that the construction of the injection tube 8 can obey any one of a different number of systems known for this type of technical problem.

A flash system 11 which keeps constant the pressure inside the reactor 7 is coupled to the outlet end flange of the reactor. Such flash system comprises, basically, a restriction or pressure regulating valve, with a manual or automatic adjustment making it possible to maintain the desired reactor internal pressure.

On passing through the flash system 11, the mixture is subject to an abrupt drop in pressure to atmospheric pressure and a consequent cooling, thus allowing the hydrolysis reaction to be completed.

In the illustrated installation, the hydrolyzed product passes through a hydrocyclone 12 which separates the solid portions discharged through 13, the liquid portions withdrawn at 14 and the gaseous portions which rise up through the packed column 15, pass through the condenser 16 and go out in a liquid form at 17.

Hidrocyclone 12 can be replaced by a cyclone and, in this case, the liquid portion will go out together with the solid portion at 13, being pumped to the filter 18 which will effect the separation of the solid portion at 19 and of the liquid portion at 20. Whichever solution is adopted, the gaseous portion after being condensed will continue to a recovery system for methanol, furfural and acetic acid.

The solid portion, composed principally of lignin, can be used in its natural form or converted to coke.

The liquid portion which constitutes a solution of sugars, must undergo neutralisation, followed by anaerobic fermentation to produce ethanol or by aerobic fermentation which will give rise to unicellular protein.

We claim:

1. A process for obtaining ethanol by continuous acid hydrolysis of cellulosic materials, consisting essentially of (a) providing an aqueous homogenized pulp of cellulosic materials containing about 3 to 30% of solids by weight;
    (b) providing a tubular reactor having an inlet at one end therof and an outlet at the opposite end thereof;
    (c) maintaining a constant pressure within the reactor by pumping said pulp in a substantially continuous manner into said tubular reactor through the inlet and while controlling outflow of said pulp at the outlet end of said reactor, said pressure ranging between about 10 and about 40 kg/cm$^2$;
    (d) electrically heating said pulp to a temperature ranging between about 160° C. and about 250° C. prior to pumping said pulp into said reactor;
    (e) providing a point of acid addition into said reactor, said point being continually adjustable longitudinally from the inlet of said reactor towards the outlet of said reactor;
    (f) substantially continuously adding into said pressurized and heated pulp concentrated acid selected from the group consisting of sulfuric, sulfurous, hydrochloric, and phosphoric acid in an amount sufficient to cause a hydrolysis reaction to occur;
    (g) discharging in a substantially continuous manner through the outlet end of said reactor said hydrolyzed cellulosic material;
    (h) during said process, adjusting the retention time of said acid and said cellulosic material to be maintained at an optimum for said hydrolysis reaction, by longitudinally adjusting said point of acid addition and by regulating the rate of said discharge;
    (i) immediately upon discharge from the reactor, subjecting the hydrolyzed pulp to an abrupt pressure drop and cooling it, thereby causing the evaporation of volatile components from said pulp and completing said hydrolysis reaction;
    (j) subsequently separating the pulp into a solid residue and an aqueous solution supernatant;
    (k) neutralizing and fermenting said supernatant to obtain ethanol; and
    (l) recovering said volatile components evaporated in said step (i).

2. A process according to claim 1, wherein the reaction time of the cellulosic material pulp inside the reactor is about 20 to 300 seconds.

3. A process according to claim 1, wherein the concentrated acid is sulfuric acid, said acid being added in an amount such that, when diluted by the water of the cellulosic material pulp, it is present in a concentration of about 0.1 to 3%.

* * * * *